United States Patent [19]

Schaffner et al.

[11] 4,015,007
[45] Mar. 29, 1977

[54] HETEROCYCLIC SPIRO COMPOUNDS

[75] Inventors: Karl Schaffner, Binningen; Alex Meisels, Basel, both of Switzerland; Jean Claude Roger, New York, N.Y.; Claus D. Weis, Pfeffingen, Switzerland

[73] Assignee: Ciba-Geigy Corporation, Ardsley, N.Y.

[22] Filed: July 23, 1975

[21] Appl. No.: 598,304

Related U.S. Application Data

[62] Division of Ser. No. 356,545, May 2, 1973, Pat. No. 3,914,222.

[30] Foreign Application Priority Data

May 4, 1972 Switzerland .................. 6613/72

[52] U.S. Cl. .................................. 424/267
[51] Int. Cl.$^2$ ............................. C07D 221/20
[58] Field of Search ............. 260/293.56, 326.5 R, 260/326.8, 326.85; 424/267, 274

[56] References Cited

UNITED STATES PATENTS 2,931,805   4/1960   Weinstock ............... 260/239.3

*Primary Examiner*—G. Thomas Todd
*Attorney, Agent, or Firm*—Joseph G. Kolodny; John J. Maitner; Theodore O. Groeger

[57] ABSTRACT

Compounds of the class of spiro[norbornane-2,3'-piperidines], spiro[bicyclo[2.2.2]octane-2,3'-piperidines], and corresponding spiro-pyrrolidine derivatives which are unsubstituted at the ring nitrogen atom or substituted by neutral or basic radicals, and the pharmaceutically acceptable acid addition salts of these new compounds possess valuable pharmacological properties and are active ingredients for pharmaceutical compositions. In particular, these new compounds have an antiviral activity. Specific embodiments are (1RS,2RS,4SR)-spiro[norbornane-2,3'-piperidine]-hydrochloride and 1'-[2-(2-azaspiro[5.5]undec-2-yl)-ethyl]-spiro[bicyclo[2.2.2]octane-2,3'-piperidine]-dihydrochloride.

6 Claims, No Drawings

HETEROCYCLIC SPIRO COMPOUNDS

This is a division of Ser. No. 356,545, filed May 2, 1973, now U.S. Pat. No. 3,914,222.

The present invention relates to processes for the production of new heterocyclic spiro compounds and their acid addition salts, to these new substances themselves, as well as to pharmaceutical preparations containing them and to the use thereof.

The compounds according to the invention correspond to the general formula I

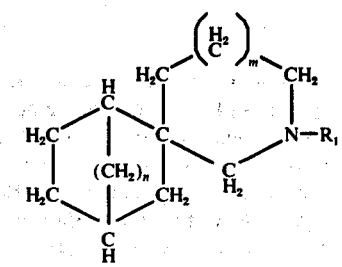

wherein $R_1$ represents hydrogen, an alkyl group having at most 6 carbon atoms, an optionally chlorine-substituted hydroxyalkyl group in which the bonds to the ring nitrogen atom, to the hydroxy group, and to the optionally present chlorine atom proceed from different carbon atoms, and which contains at least 2 or 3, and at most 6, carbon atoms, an alkenyl group having 3 to 6 carbon atoms, the 2-propynyl group, a phenyl-(lower alkyl) group optionally mono- to trisubstituted by halogen, lower alkyl or alkoxy groups, or a basic radical of the partial formula I a

wherein alk stands for a nongeminal, bivalent, saturated aliphatic hydrocarbon radical having 2 to 5 carbon atoms, or for the 2-hydroxy-trimethylene radical, $R_2$ and $R_3$ have the meanings given for $R_1$, with exception of the radical of the partial formula Ia, and can together also represent a tetramethylene to hexamethylene radical, optionally substituted by lower alkyl groups, the ethyleneoxyethylene radical, or a tetra- or pentamethylene radical substituted, for its part, in the 2-position by the tetramethylene, pentamethylene, 1,4-methanopentamethylene or 1,4-ethanopentamethylene radical, $m$ represents 0 or 1, and $n$ represents 1 or 2.

In the compounds of the general formula I, $R_1$ as the alkyl group or alkenyl group is, for example, the methyl, propyl, isopropyl, butyl, isobutyl, pentyl, isopentyl, neopentyl or hexyl group, but preferably the ethyl group; as the alkenyl group it is, for example, the allyl, 1-methylallyl, 2-methylallyl, 2-butenyl, 1,2-dimethylallyl, 3-methyl-2-butenyl, 2-pentenyl, 2,3-dimethyl-2-butenyl or 2-hexenyl group; and as an optionally chlorine-substituted hydroxyalkyl group, $R_1$ is, for example, the 2-hydroxyethyl, 2-hydroxypropyl, 3-hydroxypropyl, 2-hydroxy-, 3-hydroxy- or 4-hydroxybutyl, 2-methyl-3-hydroxypropyl, 2-hydroxy- or 5-hydroxypentyl, 2,2-dimethyl-3-hydroxypropyl, 2-hydroxyhexyl, 6-hydroxyhexyl, 1-methyl-4-hydroxypentyl, 3-chloro-2-hydroxybutyl, 4-chloro-2-hydroxybutyl, 3-chloro-2-hydroxy-2-methylpropyl or 5-chloro-2-hydroxypentyl group, and preferably the 3-chloro-2-hydroxypropyl group. Optionally substituted phenyl-(lower alkyl) groups contain in their lower alkyl group preferably 1 to 4 carbon atoms and are, for example, the phenethyl, α-methylbenzyl, 2-phenylpropyl, α-methylphenethyl, 2-phenylbutyl or 4-phenylbutyl group, and preferably the benzyl or 3-phenylpropyl group, as well as corresponding groups substituted as defined in the phenyl radical, such as, e.g. the o-, m- or p-fluorobenzyl group, the o-, m- or p-chlorobenzyl group, the 2,4-, 2,5-, 2,6- or 3,4-dichlorobenzyl group, the o-, m- or p-bromobenzyl group, the o-, m- or p-methylbenzyl group, the p-ethylbenzyl or p-iso-propylbenzyl group, the o-, m- or p-methoxybenzyl group, the p-ethoxybenzyl, p-propoxybenzyl, p-isopropoxybenzyl, p-butoxybenzyl, 2,4-dimethoxybenzyl, 3,4-dimethoxybenzyl or 3,4,5-trimethoxybenzyl group, whereby the 3,4-dichlorobenzyl group is of particular importance.

As a nongeminal, bivalent, saturated aliphatic hydrocarbon radical, alk in the partial formula Ia is, for example, the propylene, tetramethylene, 2-methyltrimethylene, 1- or 3-methyltrimethylene, pentamethylene or 2,2-dimethyltrimethylene group, and preferably the trimethylene and particularly the ethylene group. The symbols $R_2$ and $R_3$ can represent, for example, the groups mentioned above as examples for $R_1$ and are, in particular, hydrogen atoms, methyl or benzyl groups. $NR_2R_3$ can be, for example, the 1-pyrrolidinyl, piperidino, 2-methylpiperidino, 2,6-dimethylpiperidino, hexahydro-1H-azepin-1-yl, 2-azaspiro[4.4]non-2-yl, 2-azaspiro[4.5]dec-2-yl, 7-azaspiro[4.5]dec-7-yl, 2-azaspiro[5.5]undec-2-yl, spiro[norbornane-2,3'-pyrrolidin]-1'-yl, spiro[norbornane-2,3'-piperidin]-1'-yl, spiro[bicyclo[2.2.2]octane-2,3'-pyrrolidin]-1'-yl or spiro[bicyclo[2.2.2]octane-2,3'-pyrrolidin]-1'-yl group, whereby the 2-azaspiro[5.5]undec-2-yl group is of special importance.

The compounds of the general formula I and their addition salts with inorganic and organic acids possess valuable pharmacological properties, particularly antiviral activity, and at the same time have relatively low toxicity. Compounds of particular importance are compounds of the general formula I wherein $m$ is 1 and $n$ 1 or 2. Preferred compounds within this group are those in which $R_1$ is hydrogen or an ethyl group and, in particular, a 3,4-dichlorobenzyl or 3-phenylpropyl group, or stands for a group of the partial formula I a wherein alk represents the trimethylene, 2-hydroxytrimethylene and, in particular, the ethylene radical, $R_2$ represents hydrogen or a methyl or benzyl group, and $R_3$ represents hydrogen or a methyl group, or $R_2$ and $R_3$ together represent a tetramethylene, pentamethylene or 2,2-(1,4-methanopentamethylene)-pentamethylene group and, in particular, a 2,2-pentamethylene-pentamethylene group which forms, together with the adjacent nitrogen atom, the 2-azaspiro[5.5]undec-2-yl radical. The antiviral activity of compounds of the general formula I and of their acid addition salts, such as (1RS,2RS,4SR)-spiro[nonbornane-2,3'-piperidine]-hydrochloride, 1'-(3,4-dichlorobenzyl)-(1RS,2RS,4SR)-spiro[norbornane-2,3'-piperidine]-hydrochloride, 1'-(3-phenylpropyl)-(1RS,2RS,4SR)- spiro[norbornane-2,3'-piperidine]-hydrochloride and 1'-(2-(2-azaspiro[5.5]undec-2-yl)-ethyl]-spiro[bicyclo[2.2.2]octane-2,3'-piperidine]-dihydrochloride, was determined, for example, on rhino-viruses (grown in biocytocultures) of the strains Type 2 (HGP), Type 39 (209), Type 51 (FO 1) and others. Furthermore, compounds of the general formula I and their acid addition salts also exhibit antiviral activity in the case of RS-viruses, influenze-A2-viruses and adeno-viruses.

The antiviral activity of the compounds of the general formula I and of their pharmaceutically acceptable acid addition salts, as well as the favourable therapeutic index, distinguishes these new substances as active substances that can be used for the prevention and treatment of virus infections of mammals, particularly of diseases of the respiratory tract, such as nasal catarrh, influenza and acute bronchitis.

The new compounds of the general formula I and their acid addition salts are produced by a process in which a corresponding dicarboxylic acid imide of the general formula II

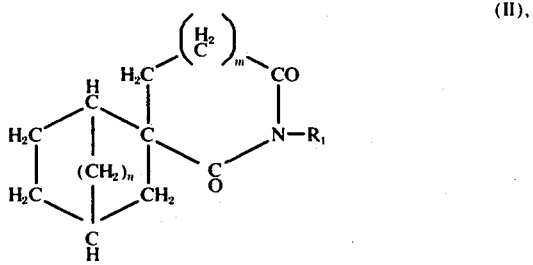

wherein $R_1$, $m$ and $n$ have the meanings given under formula I, is reduced by means of a complex hydride; and, optionally, the obtained compound of the general formula I converted into an addition salt with an inorganic or organic acid.

The reduction of imides of the general formula II is effected, for example, by means of lithium aluminium hydride or diborane in an ethereal solvent such as diethyl ether, tetrahydrofuran, dibutyl ether or diethylene glycol diethyl ether, or in mixtures thereof, at temperatures of between ca. 20° and 100° C or the boiling temperature of the employed reaction medium. The diborane can either be separately produced and then introduced, or be formed in situ from sodium borohydride and borotrifluoride-etherate.

The imides of the general formula II can be produced by addition of a 2-methyleneglutarimide or methylenesuccinimide, substituted in the imide group by $R_1$, to cyclopentadiene or 1,3-cyclohexadiene; and hydrogenation of the double bond remaining. The diene-syntheses are performed, for example, at temperatures of ca. 150° to 160° C in the presence or absence of a diluent, such as, e.g. benzene, in a closed vessel and with a reaction time of ca. 16–36 hours, whereby approximately equimolar amounts of diene and dienophile are used. It is advantageous in some cases to employ, instead of an imide, a precursor thereof to serve as dienophile, and to form the optionally substituted imide group not until after the performed diene synthesis. For example, the aforementioned cyclic diene is firstly reacted with 2-methyleneglutaronitrile to give 2-cyano-5-norbornene-2-propionitrile or 2-cyano-bicyclo[2.2.2]oct-5-ene-2-propionitrile. By catalytic hydrogenation of the remaining double bond of these dinitriles, e.g. in the presence of platinum dioxide at room temperature and under normal pressure in a lower alkanol, and boiling of the hydrogenation product with conc. hydrochloric acid, there are obtained the imides embraced by the general formula II wherein $R_1$ is a hydrogen atom, $m$ denotes 1 and $n$ denotes 1 or 2. Moreover, it is also possible, with the use of free methylenesuccinic acid or 2-methyleneglutaric acid as dienophiles, to firstly produce the dicarboxylic acids on which the imides of the general formula II are based, to convert these by boiling with acetic anhydride into their inner anhydrides, and to react the last-named with compounds of the general formula II a

wherein $R_1$ has the meaning given under formula I, for example, in glacial acetic acid at its boiling temperature, to give imides of the general formula II, Imides without N-substituent are obtained also be conversion of the aforementioned dicarboxylic acids into their diammonium salts and heating of these until the release of ammonia and water is completed. Mentioned as a further possibility for the production of the dicarboxylic acids is also the hydrolysis of the corresponding dinitriles, of which some have already been referred to above, with moderately concentrated sulphuric acid or with lower-alkanolic potassium hydroxide solution; and as a further means of arriving at the corresponding anhydrides, their direct production by diene synthesis with the use of methylenesuccinic acid anhydride or 2-methylene-glutaric acid anhydride. In addition, imides of the general formula II wherein $R_1$ is not hydrogen can be obtained also by reaction of alkali metal salts of the imides embraced by the general formula II, and unsubstituted in the imide group, with reactive esters of compounds of the general formula III given below.

According to a second process, compounds of the general formula I wherein $R_1$ is not hydrogen are produced by the reaction of a compound of the general formula I b embraced by the general formula I:

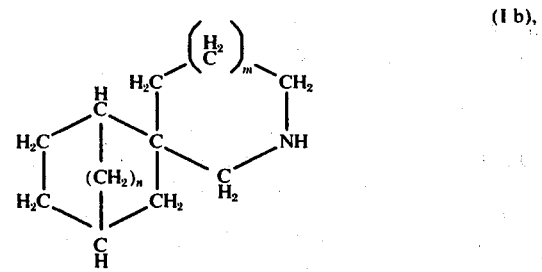

wherein $m$ and $n$ have the meanings given under formula I, with a reactive ester of a compound of the general formula III

wherein $R_1'$ has the meaning given for $R_1$ under formula I, with the exception of hydrogen, in the presence of an acid-binding agent, or with formaldehyde in the presence of formic acid; and, optionally, the conversion of the obtained compound embraced by the general formula I into an addition salt with an inorganic or organic acid.

Suitable reactive esters of compounds of the general formula III are, for example, arene- and alkanesulphonic acid esters, such as benzenesulphonic acid ester, p-bromobenzenesulphonic acid ester, P-toluenesulphonic acid ester or methanesulphonic acid ester, as well as, in particular, hydrohalic acid esters, such as, e.g. bromides and chlorides; and also, as specific sulphuric acid esters, dimethylsulphate and diethylsulphate. An excess of the basic compound to be reacted of the general formula Ib can serve as the reaction medium and, at the same time, as an acid-binding agent. The reaction is preferably performed, however, in an organic solvent, such as ethanol, butanone, dioxane or dimethylformamide, whereby, instead of excess compound of the general formula Ib, another acid-binding agent, e.g. a tertiary organic base such as, e.g. ethyl-diisopropylamine, or, in particular, inorganic basic substances, such as, e.g. potassium or sodium carbonate, can be used for the binding of the liberated acid. Both the starting materials of the general formula I b, and the reactive esters of compounds of the general formula III which contain an amino group as defined, can be used also in the form of their acid addition salts, from which the bases are liberated in situ by the corresponding amount of an acid-binding agent, such as, e.g. potassium carbonate. The reactions are performed preferably at temperatures of between ca. 50° and 180° C and, depending on the boiling temperature of the employed ester and of the solvent, if necessary in a closed vessel. For the reaction with formaldehyde in the presence of formic acid, the procedure entails, for example, the heating of a compound of the general formula I b in a mixture of formaldehyde and formic acid for ca. ½ to 5 hours at temperatures of between ca. 70° and 100° C.

The compounds of the general formula I b are, in their turn, preferably produced according to the first-mentioned process by the reduction of the corresponding imides of the general formula II. Reactive esters of compounds of the general formula III are known in large numbers; others can be produced by methods analogous to those for the known ones.

According to a third process, compounds of the general formula I wherein $R_1$ is not hydrogen, as well as their acid addition salts, are obtained by the reduction, by means of a complex hydride, of a compound of the general formula IV

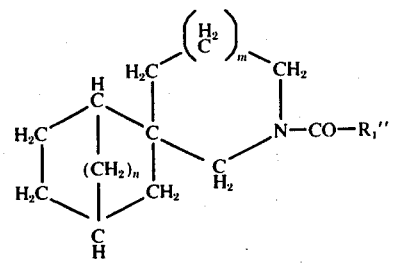

wherein
$R_1''$ represents a radical lessened by a methylene group, but otherwise corresponding to the definition for
$R_1$ given under formula I,
and $m$ and $n$ have the meanings given under formula I, or of a compound of the general formula V

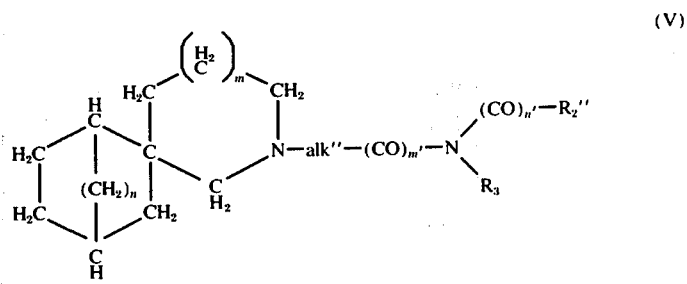

wherein
$m'$ and $n'$ each represent 0 or 1 and have a sum always equal to 1,
$alk''$ represents a bivalent, saturated aliphatic hydrocarbon having $(2-m')$ to $(5-m')$ carbon atoms, and
$R_2''$ represents a radical lessened by the group $(CH_2)_n$ but otherwise corresponding to the definition for $R_2$ given under formula I, or, where $n'$ is 1, can represent a lower alkoxy group,
and $R_3$, $m$ and $n$ have the meanings given under formula I; and, optionally, the conversion of the obtained compound embraced by the general formula I into an addition salt with an inorganic or organic acid.

The reduction can be performed, for example, with lithium aluminium hydride or with diborane under the same conditions as for the reduction of the dicarboxylic acid imides of the general formula II. The starting materials of the general formula IV can be produced from compounds of the general formula I b by the usual methods; particularly by reaction with carboxylic acid halides or -anhydrides in the presence of tertiary organic bases, such as pyridine. Compounds of the general formula IV of which the radical $R_1''$ contains a primary, secondary or tertiary amino group are produced from the compounds of the general formula I b preferably in two steps, in that the stated compounds are firstly reacted with halogenalkanoyl halides having 2 to 5 carbon atoms to give corresponding N-halogenalkanoyl derivatives, and these allowed to react with a compound of the formula VII given below or, if necessary, with an N-alkali metal derivative of such a compound.

Starting materials of the general formula V wherein $m'$ denotes 1 and $n'$ denotes 0 are obtained, for example, by reaction of compounds of the general formula I b with halogenalkaneamides, such as, e.g. halogenacetamides, of which the amide group is optionally substituted corresponding to the definition for $R_2$ and $R_3$, in the presence of acid-binding agents analogously to the second process for the production of compounds of the general formula I. Starting materials of the general formula V in which $m'$ denotes 0 and $n'$ denotes 1 are obtained, e.g. by acylation of primary or secondary amines embraced by the general formula I c given below, i.e. compounds with hydrogen as $R_2$ and/or $R_3$, with halides or anhydrides of carboxylic acids of the general formula V a $$R_2''' - CO - OH \qquad (V\ a)$$

wherein $R_2'''$ represents a radical lessened by a methylene group, but otherwise corresponding to the definition for $R_2$, or with lower chloroformic acid alkyl esters, in the presence of acid-binding agents.

According to a fourth process, the compounds (embraced by the general formula I) of the general formula I c given below and their acid addition salts are produced by the reaction of a reactive ester of a compound of the general formula VI

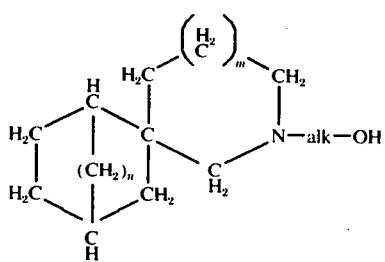

(VI), wherein alk, m and n have the meanings given under formula I, with a compound of the general formula VII

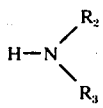

(VII)

wherein $R_2$ and $R_3$ have the meanings given under formula I, or with an alkali metal compound of a secondary amine embraced by the general formula VII; and, optionally, the conversion of the obtained compound embraced by the general formula I into an addition salt with an inorganic or organic acid. The compounds obtained by this process correspond to the general formula I c

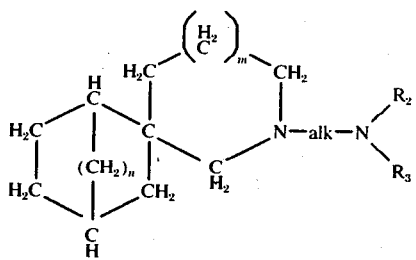

(I c)

wherein alk, $R_2$, $R_3$, m and n have the meanings given under formula I.

Suitable reactive esters of compounds of the general formula IV are, for example, sulphonic acid esters such as the p-toluenesulphonic acid ester and the methanesulphonic acid ester, and particularly hydrohalic acid esters such as, e.g. bromides and chlorides. An excess of the basic compound of the general formula VII to be reacted can serve as the reaction medium and, at the same time, as the acid-binding agent. Provided that the reactive esters to be reacted are based on compounds having a primary hydroxy group, the reaction can be carried out in most cases already at temperatures between 50° and 120° C. Depending on the boiling temperature of the compound of the general formula VII, the reaction is carried out if necessary in a closed vessel. It can also be performed in a solvent such as, ethanol, butanone, dioxane or dimethylformamide, whereby for the binding of the liberated acid it is possible to use, instead of excess compound of the general formula VII, also tertiary organic bases such as, for example, ethyl-diisopropylamine, or inorganic basic substances such as, for example, sodium and potassium carbonate. In the case of reactions of reactive esters of compounds of the general formula VI of which the hydroxy group is not primary-bound with amines of the general formula VII, higher temperatures of between ca. 100° and 180° C are in most cases necessary, and with the use of ammonia or low-boiling amines and/or the use of low-boiling solvents, closed vessels required. The N-alkali metal compounds, which can optionally be used instead of the free secondary amines, are, for example, formed in situ, e.g. by reaction with sodium amide, sodium hydride or lithium amide, in an inert organic solvent, such as, e.g. benzene or toluene, and subsequently directly reacted.

The compounds of the general formula VI in their turn are produced, for example, by reaction of compounds of the general formula Ib with halogenalkanols having 2 to 5 carbon atoms in the presence of acid-binding agents, such as potassium carbonate or triethylamine, in ethanol at the boiling temperature, analogously to the secondmentioned process for the production of compounds of the general formula I, or moreover by reaction of compounds of the general formula Ib with vic. epoxyalkanes having 2 to 5 carbon atoms, such as, e.g. ethylene oxide. The reactive esters required as direct starting materials can be produced from the compounds of the general formula VI, e.g. by reaction with thionyl chloride, phosphorus tribromide, p-toluenesulphochloride or methanesulphochloride; it is also possible, however, to react compounds of the general formula Ib direct with equimolar amounts of bis-halogenalkanes or p-toluenesulphonic acid halogenalkyl esters, in the presence of acid-binding agents to give the corresponding N-halogenalkyl compounds as reactive esters of compounds of the general formula VI.

Compounds of the general formula I c (embraced by the general formula I) given above wherein $R_2$ and $R_3$ are hydrogen atoms, and their acid addition salts, can be produced by a fifth process comprising the reduction of a nitrile of the general formula VIII

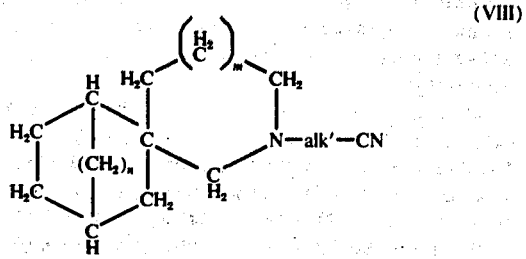

(VIII)

wherein alk' represents a bivalent, saturated aliphatic hydrocarbon radical having 1 to 4 carbon atoms, and $m$ and $n$ have the meanings given under formula I; and, optionally, the conversion of the obtained compound embraced by the general formula I into an addition salt with an inorganic or organic acid. The nitriles of the general formula VIII can be reduced by chemical methods, especially by means of complex hydrides, such as lithium aluminium hydride or diborane, in ethereal solvents, such as tetrahydrofuran or diethyl ether, at temperatures of between ca. 20° and 100° C. Likewise suitable is catalytic hydrogenation, which is performed, e.g. in the presence of Raney nickel in an organic solvent such as methanol or ethanol, at elevated temperatures and under elevated pressure, e.g. at 50° to 100° C and under ca. 100 to 200 bars, and preferably in the presence of ammonia. The nitriles of the general formula VIII can be produced, for example, by reaction of reactive esters of compounds of the general formula VI with potassium or sodium cyanide in the usual manner.

The compounds of the general formula I c given above and embraced by the general formula I, in which formulae $R_2$, alk, m and n have the meanings defined under formula I, and $R_3$ has the meaning given there with the exception of hydrogen, and their acid addition salts are produced according to a sixth process comprising the reaction of a compound of the general formula I d embraced by the general formula I

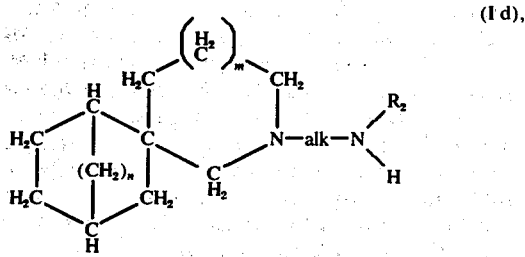

(I d), wherein $R_2$, alk, $m$ and $n$ have the meanings given under formula I, with a reactive ester of a compound of the general formula IX

$R_3' - OH$ (IX), wherein $R_3'$ represents a radical corresponding to the definition for $R_3$ given under the general formula I, with the exception of hydrogen, in a molar ratio chosen to suit the number of hydrogen atoms to be replaced, or with formaldehyde in formic acid in an amount sufficient for the replacement of all the hydrogen atoms bound to the nitrogen atom of the side chain; and, optionally, the conversion of the obtained compound embraced by the general formula I into an addition salt with an inorganic or organic acid. Types of reactive esters of compounds of the general formula IX which can be used are the types mentioned in the case of the second process for the production of compounds of the general formula I, with the same reaction conditions, acid-binding agents and solvents. The mono- or dimethylation with formaldehyde and formic acid to form a tertiary amine embraced by the general formula I c can be performed under the conditions given for the second process for the production of compounds of the general formula I.

Compounds of the general formula I wherein $R_1$ represents an alkyl group substituted in the 2-position by a hydroxy group and optionally in another position by chlorine and having at most 6 carbon atoms, or a 2-hydroxypropyl group substituted in the 3-position by the group $NR_2R_3$ wherein $R_2$ and $R_3$ have the meaning given under formula I, and m and n have the meanings given under formula I, and their acid addition salts are produced according to a seventh process comprising the reaction of a compound of the general formula I b given above, wherein M and n have the meanings given under formula I, with a compound of the general formula X

(X)

wherein $R_4$ represents hydrogen, an optionally chlorine-substituted alkyl group having at most 4 carbon atoms, or a methyl group substituted by the group $NR_2R_3$ wherein $R_2$ and $R_3$ have the meanings given under formula I, and $R_5$ represents hydrogen, or, if $R_4$ is an alkyl group optionally substituted by chlorine, can represent an alkyl group containing, together with $R_4$, at most 4 carbon atoms;

and, optionally, the conversion of the obtained compound embraced by the general formula I into an addition salt with an inorganic or organic acid.

The reaction according to the process is performed in the presence or absence of an inert organic solvent at temperatures from ca. 0° C, preferably at room temperature or at moderately elevated temperature. On account of the exothermic reaction with the use of particularly reactive starting materials of the general formula X, cooling is to be applied where necessary. The application of the mildest possible conditions is particularly of importance if the radical $R_4$ of the compound of the general formula X contains a chlorine atom; otherwise the reaction can be carried out if necessary also at higher temperatures up to ca. 150° C. It is possible to use as solvents, e.g. lower alkanols such as, for example, ethanol or methanol, lower alkoxyalkanols such as 2-methoxyethanol, or ethers and ethereal solvents such as ethylene glycol dimethyl ether, diethylene glycol dimethyl ether, tetrahydrofuran or dioxane; and the reaction can be performed if necessary in a closed vessel, or accelerated by the addition of potassium carbonate.

Starting materials of the general formula X having a lower alkyl or chloroalkyl group as $R_4$, and hydrogen or a lower alkyl group as $R_5$, are known in appreciable numbers, and others are producible analogously to the known ones. Starting materials of the general formula X having a radical substituted by the group $NR_2R_3$ as $R_4$ and a hydrogen atom as $R_5$ are obtained, for example, by the treatment of compounds of the general formula X a

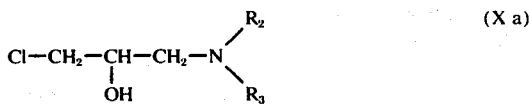

wherein $R_2$ and $R_3$ have the meanings given under formula I with potassium or sodium hydroxide, or by reaction of N-alkali metal derivatives of amines of the general formula VII given above, particularly of cyclic compounds embraced by this formula such as, e.g. compounds of the earlier given general formula I b wherein m and n have the meanings given under formula I, with epichlorohydrin (1-chloro-2,3-epoxypropane). Some compounds of the general formula X a are known, and further such compounds obtainable, e.g. analogously to the above-mentioned process for the production of compounds of the general formula I by reaction of epichlorhydrin with amines of the earlier given general formula VII.

The present invention comprises also such modifications of the above mentioned processes, as well as of the preceding steps mentioned subsequent to these, where a process is interrupted at a particular stage, or where a compound occurring as an intermediate at a certain stage is taken as the starting material and the uncompleted stages performed, or where a starting material is formed under the reaction conditions or is optionally used in the form of a salt. The required starting materials can be used either as racemates or as isolated optical antipodes. Instead of using specific racemates, it is also possible to use, where advantageous, e.g. if the conditions for separation into individual racemates and, if desired, into individual optically active antipodes in the case of the final materials are more favourable than in the case of the starting materials or intermediates thereof, mixtures of racemates. Such starting materials too can be optionally used in the form of salts.

The new heterocyclic spiro compounds of the general formula I obtained by the process according to the invention are optionally converted, in the usual manner, into their addition salts with inorganic and organic acids. For example, the acid, or a solution thereof, desired as the salt component is added to a solution of a compound of the general formula I in an organic solvent, such as diethyl ether, acetone, dioxane, methanol or ethanol; and the salt, which has precipitated directly or after addition of a second organic liquid such as, e.g. diethyl ether to methanol or acetone, separated.

Administration of the new heterocyclic spiro compounds of the general formula I and their pharmaceutically acceptable acid addition salts can be effected, in dosage units appropriate for the purpose, particularly orally, rectally or parenterally, for example, intramuscularly or intravenously, or locally, especially by way of the mucous lining of nose, mouth and throat, or by way of the respiratory tracts. In general, the free bases are applied in daily doses of 0.1 – 10 mg per kg of body weight; the dosage however in the case of local administration can optionally be appreciably lower. The same dosage amounts apply also to the pharmaceutically acceptable acid addition salts of the heterocyclic spiro-compounds of the general formula I; but where the acid component constitutes a considerable part of the total active substance the doses are optionally increased accordingly.

Suitable active substances of antiviral pharmaceutical preparations according to the invention are, besides the free basis of the general formula I, e.g. their addition salts with hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

Suitable dosage units, such as dragees, tablets, capsules, suppositories or ampoules, contain as active substance 1–100 mg, preferably 5–50 mg of a heterocyclic spiro compound of the general formula I or of a pharmaceutically acceptable acid addition salt thereof. A further possibility is the application of suitable amounts of preparations not administered as dosage units, such as syrups, sprays, tinctures aerosols, ointments or powders.

The content of active substances in dosage units for oral administration is preferably between 10% and 90%. Such dosage units are prepared by the combination of the active substance with, for example, solid pulverulent carriers, such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium or calcium stearate, or polyethylene glycols, to form tablets or dragee cores. The dragee cores are coated with, for example, concentrated sugar solutions which may also contain, e.g. gum arabic, talcum and/or titanium dioxide; or with a lacquer dissolved in readily volatile organic solvents or solvent mixtures. Dyestuff can be added to these coatings in order, for example, to facilitate identification of the various doses of active substance. Further suitable oral dosage units are hard capsules made from gelatine, as well as soft closed capsules made from gelatine and a softener such as glycerin. The hard capsules contain the active substance preferably as a granulate in admixture with lubricants such as talcum or magnesium stearate; and optionally stabilisers such as sodium metabisulphite ($Na_2S_2O_5$) or ascorbic acid. The active substance in soft capsules is preferably dissolved or suspended in suitable liquids, such as liquid polyethylene glycols, to which likewise stabilisers may be added.

Suitable dosage units for rectal administration are, for example, suppositories consisting of a combination of an active substance with a suppository foundation substance based on natural or synthetic triglycerides (e.g. cocoa butter), polyethylene glycols or suitable higher fatty alcohols; and gelatine rectal capsules containing a combination of the active substance with polyethylene glycols.

Ampoule solutions for parenteral administration, especially intramuscular or intravenous administration, contain, for example, a compound of the general formula I in a concentration preferably of 0.5 – 5% as an aqueous dispersion prepared with the aid of the usual solubility-promoting agents and/or emulsifiers, as well as optionally stabilising agents; or preferably an aqueous solution of a pharmaceutically acceptable, water-soluble acid addition salt of a compound of the general formula I.

For liquids for oral administration, such as syrups and elixiers, the concentration of the active substance is so adjusted that a single dose can be easily measured out, e.g. as the content of a teaspoon or of a measuring-spoon, e.g. 5 ml, or as a multiple of these volumetric amounts. Suitable as syrups are, for example, solutions of water-soluble acid addition salts, or suspensions of insoluble but absorbable acid addition salts, in aqueous solutions of sugars and/or alkane polyols, such as unrefined sugar or sorbitol or glycerin, flavourings and aromatics, as well as optionally preservatives and stabilisers. Elixiers are aqueous-alcoholic solutions of a compound of the general formula I or of pharmaceutically acceptable salts thereof, which likewise may contain the additives mentioned in the case of the syrups. Further oral preparations which may be mentioned are dropping solutions, which in most cases contain a fairly high alcohol content and, at the same time, a fairly high active-substance content, so that a single dose can be measured out, for example, as 10 to 50 drops.

The following examples (a) to (g) are to illustrate the production of some typical preparations, but these do not in any way represent the only forms of such preparations. In place of the given active substances contained therein, others may also be used, e.g. the further compounds of the general formula I described in the examples, particularly in the form of their acid addition salts.

a. An amount of 250.0 g of 1'-[2-(2-azaspiro[5.5]undec-2-yl)-ethyl]-spiro[bicyclo[2.2.2]octane-2,3'-piperidine]dihydrochloride is mixed with 550 g of lactose and 292.0 g of potato starch; the mixture is moistened with an alcoholic solution of 8 g of gelatine, and granulated through a sieve. The obtained granulate is dried and additions are then made to it of 60.0 g of potato starch, 60.0 g of talcum, 10.0 g of magnesium stearate and 20.0 g of colloidal silicon dioxide; the mixture is pressed to form 10,000 tablets each weighing 125 mg and each containing 25 mg of active substance; if desired, these can be provided with grooves to facilitate a more precise adjustment of the dosage amount.

b. A granulate is produced from 250.0 g of (1RS,2RS,4SR)-spiro[norbornane-2,3'-piperidine]-hydrochloride, 379.0 g of lactose and the alcoholic solution of 6.0 g of gelatine; the said granulate is then dried and additions are made to it of 10.0 g of colloidal silicon dioxide, 40.0 g of talcum, 60.0 g of potato starch and 5.0 g of magnesium stearate; the mixture is subsequently pressed to form 10,000 dragee cores. These are afterwards coated with a concentrated syrup made from 533.5 g of crystallised saccharose, 20.0 g of shellac, 75.0 g of gum arabic, 250.0 g of talcum, 20.0 g of colloidal silicon dioxide and 1.5 g of dyestuff; the coated dragees are finally dried. The obtained dragees each weigh 165 mg and each contain 25 mg of active substance.

c. An amount of 20.0 g of (1RS,2RS,4SR)-spiro[norbornane-2,3'-piperidine]-hydrochloride is dissolved in 1500 ml of boiled, pyrogen-free water, and the solution made up with such water to 2000 ml. The solution is filtered off, filled into 1000 ampoules each of 2 ml, and then sterilised. A 2 ml ampoule contains 20 mg or 1.0% of active substance.

d. 25 g of 1'-[2-(2-azaspiro[5.5]undec-2-yl)-ethyl]-spiro]bicyclo[2.2.2]octane-2,3'-piperidine]-dihydrochloride and 1975 g of finely ground suppository foundation substance (e.g. cocoa butter) are thoroughly mixed and then melted. There are obtained from the melt, maintained homogeneous by stirring, 1000 suppositories each weighing 2.0 g and each containing 25 mg of active substance.

e. For the obtainment of a syrup containing 0.25% of active substance, a solution is prepared of 1.5 liters of glycerin, 42 g of hydroxybenzoic acid methyl ester, 18 g of p-hydroxybenzoic acid-n-propyl ester and, with gentle heating, 25.0 g of (1RS,2RS,4SR)-spiro[norbornane-2,3'-piperidine]-hydrochloride in 3 liters of distilled water; additions are then made of 4 liters of 70% sorbitol solution, 1000 g of crystallised saccharose, 350 g of glucose and an aromatic, e.g. 250 g of "Orange Peel Soluble Fluid" or Eli Lilly and Co., Indianapolis, or in each case 5 g of natural lemon aroma and 5 g of "Halb und Halb"-essence, both from the firm Haarmann und Reimer, Holzminden, Germany; the obtained solution is filtered and the filtrate subsequently made up to 10 liters with distilled water.

f. For the preparation of a dropping solution containing 1.5% of active substance, 150.0 g of (1RS,2RS,4SR)-spiro[norbornane-2,3'-piperidine]-hydrochloride and 30 g of sodium cyclamate are dissolved in a mixture of 4 liters of ethanol (96%) and 1 liter of propylene glycol. A mixture is prepared of 3.5 liters of 70% sorbitol solution with 1 liter of water, and this mixture then added to the above active-substance solution. An aromatic is subsequently added, e.g. 5 g of cough-lozenge aroma or 30 g of grapefruit essence, both from the firm of Haarmann und Reimer, Holzminden, Germany, the whole well mixed, filtered, and made up to 10 liters with distilled water.

g. For the preparation of a nasal spray containing 0.1% of active substance, an amount of 10.0 g of 1'-[2-(2-azaspiro[5.5]undec-2-yl)-ethyl]-spiro[bicyclo[2.2.2]octan-2,3'-piperidine]-dihydrochloride is dissolved in 10 liters of distilled water, and the solution filled into spray-bottles. For the prevention and treatment of the cold in the head, 2-3 spurts from a full bottle (from a partially emptied bottle more if necessary) are injected, e.g. once to three times daily, into each nostril.

The following examples illustrate the production of the new heterocyclic spiro compounds of the general formula I, as well as of new starting materials; but these examples are not meant in any way to restrict the scope of the invention. The temperatures are expressed in degrees Centigrade.

EXAMPLE 1

An amount of 50 g (0.24 mole) of spiro[bicyclo[2.2.2]octane-2,3'-piperidine]-2',6'-dione is introduced portionwise by means of a connecting tube in the course of 15–20 minutes, with stirring, into a mixture of 14 g (0.37 mole) of lithium aluminum hydride in 3 liters of abs. ether. The temperature during the addition is not to exceed 25°. The mixture is refluxed under nitrogen for 32 hours. After subsequent cooling, successive additions are made dropwise of 14 ml of water, 28 ml of 2N sodium hydroxide solution and a further 28 ml of water. The mixture is then stirred for 1 hour; it is afterwards filtered under reduced pressure and the residue subsequently well washed with ether. The filtrate is dried over sodium sulphate and concentrated by evaporation. The residue is fractionated in high vacuum to obtain spiro[bicyclo[2.2.2]octane-2,3'-piperidine], B.P. 95°–130°/0.2 Torr. From this base there is obtained, with excess ethereal hydrogen chloride solution, spiro[bicyclo[2.2.2]octane-2,3'-piperidine]-hydrochloride, M.P. 207°–208.5° (from acetone/ether).

The spiro[bicyclo[2.2.2]octane-2,3'-piperidine]-2',6'-dione serving as starting material is produced as follows:

a. A mixture of 150 g (1.88 moles) of 1,3-cyclohexadiene, 203 g (1.88 moles) of 2-methyleneglutaronitrile and 1.9 g (0.02 mole) of hydroquinone is heated in a pressure autoclave, with stirring and under a maximum pressure of 5 bars, for 20 hours at 150°. The dark brown resin obtained after cooling is rinsed with methylene chloride in a distilling flask and the solvent evaporated off. The residue is fractionated under high vacuum to obtain a sterioisomeric mixture of 2-cyano-bicyclo[2.2.2]oct-5-ene-2-propionitrile, B.P. 124°–127°/0.5 Torr.

b. An amount of 128.7 g (0.69 mole) of 2-cyano-bicyclo[2.2.2]oct-5-ene-2-propionitrile is dissolved in 1.3 liters of the purest methanol; an addition is then made of 3 g of palladium charcoal (5% Pd) and hydrogenation performed at 15°–25° under normal pressure to effect a hydrogen absorption of 90% of theory. After removal by filtration of the catalyst, the solvent is evaporated off and the residue fractionated to obtain 2-cyano-bicyclo[2.2.2]octane-2-propionitrile, B.P. 114°–116°/0.01 Torr.

c. 105.2 g (0.56 mole) of 2-cyano-bicyclo[2.2.2]octane-2-propionitrile is mixed with 1600 ml of conc. hydrochloric acid, and the mixture refluxed in a preheated oil bath, with stirring, for ten minutes. The white precipitate, which has already formed before expiration of this period of time, is filtered off after cooling of the mixture, and the filter residue washed with water until neutral. After drying in a desiccator over phosphorus pentoxide, the white crystals are sublimated at 170°/0.1 Torr to obtain spiro[bicyclo[2.2.2]octane-2,3'-piperidine]-2',6'-dione, M.P. 183°–184°.

EXAMPLE 2

An amount of 63.6 g (0.32 mole) of (1RS,2RS,4SR)-spiro[norbornane-2,3'-piperidine]-2',6'-dione is reduced, analogously to Example 1, with lithium aluminium hydride in ether, whereby (1RS,2RS,4SR)-spiro[norbornane-2,3'-piperidine], B.P. 50°–54°/0.01 Torr, is obtained. This base is converted with ethereal hydrogen chloride solution into (1RS.2RS,4SR)-spiro[norbornane-2,3'-piperidine]-hydrochloride, M.P. 157°–160° (from methanol/ether).

The required (1RS,2RS,4SR)-spiro[norbornane-2,3'-piperidine]-2',6'-dione is produced as follows:

a. 426 g (4 moles) of 2-methyleneglutaronitrile, 264 g (4 moles) of cyclopentadiene, 4 g of hydroquinone and 500 ml of benzene are heated in a pressure autoclave at 160° and under a maximum pressure of 3 bars, with stirring, for 10 hours. The mixture obtained after cooling is concentrated in vacuo (ca. 12 Torr), the residue twice extracted with 1.5 liters of petroleum ether each time and then extracted in high vacuum. The crude product is obtained as colourless oil, B.P. 115°–128°/0.03 Torr, which is dissolved in 300 ml of ethanol. On storage of this solution in a refrigerator overnight, there crystallises 2-exo-cyano-5-norbornene-2-endo-propionitrile, M.P. 40°–42°.

b. An amount of 200 g (1.16 moles) of 2-exo-cyano-5-norbornene-2-endo-propionitrile is hydrogenated analogously to Example 1 b) to obtain 2-exo-cyano-norbornane-2-endo-propionitrile, B.P. 120°–128°/0.1 Torr.

c. 52.2 g (0.30 mole) of 2-exo-cyano-norbornane-2-endo-propionitrile is refluxed, analogously to Example 1 c), with conc. hydrochloric acid, whereupon (1RS,2RS,4SR)-spiro[norbornane-2,3'-piperidine]-2',6'-dione, M.P. 154°–156° is obtained.

EXAMPLE 3

An amount of 14.3 g (0.08 mole) of (1RS,2RS,4SR)-spiro[norbornane-2,3'-pyrrolidine-2',5'-dione] is reduced, by a procedure analogous to that described in Example 1, with 4.56 g (0.12 mole) of lithium aluminium hydride in 400 ml of tetrahydrofuran to obtain (1RS,2RS,4SR)-spiro[norbornane-2,3'-pyrrolidine, B.P. 100°–102°/12 Torr. The base is converted with etheral hydrogen chloride solution into (1RS,2RS,4SR)-spiro[norbornane-2,3'-pyrrolidine]-hydrochloride, M.P. 200°–202°.

The starting material is produced as follows:

a. 650 g (5 moles) of methylenesuccinic acid (itaconic acid) and 1 g (0.0091 mole) of hydroquinone are dissolved in a mixture of 1000 ml of isopropanol and 1000 ml of water, and, with vigorous stirring, 395 g of cyclopentadiene added within 1 hour. The mixture heats up and the rate of addition must be reduced if the reaction becomes too violent. The reaction mixture is then refluxed for 7 hours with stirring and afterwards completely concentrated by evaporation. The water is removed by the residue being concentrated by evaporation three times with ethanol and twice with benzene, whereupon crude 2-carboxy-5-norbornene-2-acetic acid is obtained as an epimer mixture.

b. An amount of 257 g (1.31 moles) of crude 2-carboxy-5-norbornene-2-acetic acid mixture is dissolved in 1500 ml of benzene and the solution boiled in a water-separator until there is no further separation of water (ca. 20 ml). Additions are then made of 500 ml of abs. ethanol and 3 g of p-toluenesulphonic acid, and the liberated water removed by azeotropic distillation. (A one-meter long silver-coated column isolated with a vacuum-jacket and filled with glass spirals is required: otherwise no equilibrium can be established in the column.) After 48 hours no further aqueous phase can be separated in the water-separator. The cooled reaction mixture is poured on 500 ml of saturated sodium bicarbonate solution, and after thorough shaking the aqueous phase separated. The benzene extract is washed twice with 500 ml of saturated sodium chloride solution each time. The aqueous phases are separately washed twice with 500 ml of benzene each time. The combined solutions are dried over sodium sulphate and concentrated in vacuo (ca. 12 Torr) to obtain 2-carboxy-5-norbornene-2-acetic acid ethyl ester as an epimeric mixture.

c. 5.0 g (0.0224 mole) of a 2-carboxy-5-norbornene-2-acetic acid/ethyl ester mixture is suspended in 10 ml of water and an addition then made at 0°–5°, with stirring, of conc. sodium hydroxide solution until a phenolphthalein-alkaline reaction is obtained. There is subsequently added, likewise at 0°–5°, 1 g of sodium bicarbonate, and the mixture stirred until the sodium bicarbonate has gone into solution. A solution of 9.5 g (0.075 gram atom) of iodine and 9.1 g (0.055 mole) of potassium iodide in 30 ml of water is then added at 5°–10°, and the reaction mixture stirred for 1 hour at room temperature. Solid sodium bisulphite is now added portionwise, whereupon the initially dark mixture becomes colourless. There is subsequently added to the mixture sodium bisulphate until no further carbon dioxide is given off. Extraction is performed three times with 50 ml of methylene chloride each time, and the methylene chloride extracts are separately washed with in each case 50 ml of 5% sodium bisulphite solution and a saturated sodium bicarbonate solution and with 50 ml of water. After drying over sodium sulphate, the organic phase is concentrated in vacuo (ca. 12 Torr) to obtain 2-endo-carboxy-5-exo-iodo-6-endo-hydroxy-2-exo-norbornaneacetic acid ethyl ester, M.P. 103°–104° (from ether). The aqueous phases are washed together, acidified with conc. hydrochloric acid, and extracted three times with 200 ml of methylene chloride each time. The methylene chloride extracts are washed separately twice with 50 ml of water each time, dried over sodium sulphate and concentrated in vacuo (ca. 12 Torr). There is thus obtained, as a second reaction product, crude 2-exo-carboxy-5-norbornene-2-endo-acetic acid ethyl ester.

d. An amount of 5 g (0.023 mole) of 2-exo-carboxy-5-norbornene-2-endo-acetic acid ethyl ester is added to a solution of 5 g of sodium hydroxide in 20 ml of water and 100 ml of ethanol, and the mixture stirred for 16 hours at room temperature. The reaction mixture is afterwards concentrated in vacuo (ca. 12 Torr). The residue is dissolved in 50 ml of water and the aqueous solution extracted three times with 50 ml of methylene chloride each time. The methylene chloride extracts are extracted twice with 50 ml of water each time and subsequently discarded. The aqueous phases are combined, acidified with conc. hydrochloric acid, and extracted three times with 100 ml of methylene chloride each time. The methylene chloride extracts are washed separately with saturated sodium chloride solution and concentrated by evaporation to obtain 2-exo-carboxy-5-norbornene-2-endo-acetic acid, M.P. 152° (from water).

e. An amount of 6.0 g (0.0305 mole) of 2-exo-carboxy-5-norbornene-2-endo-acetic acid is dissolved in 120 ml of the purest methanol; there is then added 300 mg of palladium charcoal (5% Pd) and hydrogenation performed at 20°–32° under normal pressure until a hydrogen absorption of 100% of theory is effected. After the catalyst has been filtered off, the solvent is evaporated off and the residue dried in vacuo (ca. 12 Torr) to obtain 2-exo-carboxy-2-endonorbornaneacetic acid, M.P. 145°.

f. 5.83 g (0.0294 mole) of 2-exo-carboxy-2-endonorbornaneactic acid is dissolved in 31.2 ml of conc. ammonia, and the solution concentrated in vacuo (ca. 12 Torr). The dry residue is heated for 1 hour at 200°, during which time a large amount of ammonia is given off. After this period of time, the evolution of gas ceases and the reaction is finished. The cooled residue is dissolved in 50 ml of methylene chloride and the obtained solution extracted twice with 50 ml of saturated sodium bicarbonate solution each time. The aqueous extracts are washed separately twice with in each case 50 ml of methylene chloride. The organic phases are combined, dried over sodium sulphate and concentrated in vacuo (ca. 12 Torr) to obtain (1RS, 2RS, 4SR)-spiro[norbornane-2,3'-pyrrolidine-2',5'-dione], M.P. 169°–170° (from water).

EXAMPLE 4

14.3 g (0.08 mole) of (1RS, 2SR, 4SR)-spiro[norbornane-2,3'-pyrrolidine-2',5'-dione] is reduced with 4.56 g (0.12 mole) of lithium aluminium hydride in 400 ml of tetrahydrofuran analogously to Example 1, whereby (1RS, 2SR, 4SR)-spiro[norbornane-2,3'-pyrrolidine], B.P. 100°–105°/15 Torr is obtained.

The base is converted with ethereal hydrogen chloride solution into (1RS, 2SR, 4SR)-spiro[norbornane-2,3'-pyrrolidine]-hydrochloride-hydrate, M.P. 107°–108° (from benzene/ether).

The starting material is produced as follows:

a. An amount of 5.0 g (0.0143 mole) of 2-endo-carboxy-5-exo-iodo-6-endo-hydroxy-2-exo-norbornaneacetic acid ethyl ester (first reaction product of Example 3 c)] is dissolved in 168 ml of glacial acetic acid; there is then added portionwise to the solution at 10°–15°, within 10 minutes, 7 g of superpure zinc powder. The mixture is filtered and the filtrate concentrated in vacuo (ca 12 Torr). The residue is suspended in 50 ml of saturated sodium bicarbonate solution, and the suspension extracted three times with 50 ml of methylene chloride each time. The methylene chloride extracts are separately extracted once in each case with 50 ml of saturated sodium bicarbonate solution and water, dried over sodium sulphate and concentrated by evaporation: there is thus obtained a neutral product which was subjected to no further investigation. The aqueous phases are combined, washed with methylene chloride, acidified with conc. hydrochloric acid, and extracted three times with 100 ml of methylene chloride each time. The methylene chloride extracts are each washed twice with water, dried over sodium sulphate, and concentrated by evaporation to obtain crude 2-endocarboxy-5-norbornene-2-exo-acetic acid ethyl ester.

b. There is obtained, analogously to Example 3(d), 2-endocarboxy-5-norbornene-2-exo-acetic acid, M.P. 161°–162°, starting with 30 g (0.134 mole) of 2-endocarboxy-5-norbornene-2-exo-acetic acid ethyl ester and 16 g of sodium hydroxide.

c. There is obtained, analogously to Example 3(e), 2-endocarboxy-2-exo-norbornaneacetic acid, M.P. 147-157°, starting with 30 g (0.153 mole) of 2-endocarboxy-5-norbornene-2-exo-acetic acid in the presence of 1.5 g of palladium charcoal (5% Pd) after a hydrogen absorption of 99% of theory.

d. There is obtained, analogously to Example 3(f), (1RS, 2SR, 4SR)-spiro[norbornane-2',3'-pyrrolidine-2',5'-dione], M.P. 145°–146° (from water), starting with 30 g (0.151 mole) of 2-endo-carboxy-2-exo-norbornaneacetic acid and 120 ml of conc. ammonia.

EXAMPLE 5

An amount of 6.0 g (0.030 mole) of spiro[bicyclo[2.2.2]-octane-2,3'-piperidine] is dissolved in 50 ml of ethanol; additions are then made of 6.8 g (0.033 mole) of phenethylbromide and 10 g (ca. 0.07 mole) of anhydrous potassium carbonate, and the whole subsequently refluxed, with stirring, for 18 hours. The reaction mixture is filtered, and the brown filtrate concentrated in vacuo (ca. 12 Torr). The viscous residue is distributed between 100 ml of methylene chloride and 100 ml of water. The methylene chloride phase is separated, and the aqueous phase afterwards washed twice with 100 ml of methylene chloride. The combined methylene chloride solutions are dried over sodium sulphate, and then concentrated in vacuo (ca. 12 Torr). There is obtained viscous 1'-phenethylspiro[-bicyclo[2.2.2]octane-2,2'-piperidine]. This is dissolved in 50 ml of ether and there is then added to the solution, with stirring, 10 ml of saturated ethereal hydrogen chloride solution. The precipitated hydrochloride is filtered off. There is obtained, after recrystallisation from acetone, 1'-phenethyl-spiro[bicyclo[2.2.2]octane2,3'-piperidine]-hydrochloride, M.P. 263° (with decomposition).

There is obtained in an analogous manner 1'-benzyl-spiro[bicyclo[2.2.2]octane-2,3'-piperidine] and its hydrochloride, M.P. 195.5° – 197° (from acetone), starting with 6.0 g (0.034 mole) of spiro[bicyclo[2.2.-2]octane2,3'-piperidine], 6.4 g (0.037 mole) of benzyl bromide and 10 g (ca. 0.07 mole) of anhydrous potassium carbonate.

EXAMPLE 6

There is obtained, analogously to Example 5, 1'-ethyl-(1RS, 2RS, 4SR)-spiro[norbornane-2,3'-piperidine]-hydrochloride, M.P. 254°–257°, starting with 5 g (0.030 mole) of (1RS, 2RS, 4SR)-spiro[norbornane-2,3'-piperidine]5 g (0.046 mole) of ethyl bromide and 10 g (ca. 0.07 mole) of anhydrous potassium carbonate.

The following are obtained likewise analogously to Example 5:

1'-benzyl-(1RS,2RS,4SR)-spiro[norbornane-2,3'-piperidine] and its hydrochloride, M.P. 201°–204° (from methanol/ether), starting with 4.8 g (0.029 mole) of (1RS,2RS,4SR)-spiro[norbornane-2,3'-piperidine[, 6.4 g (0.037 mole) of benzyl bromide and 5.5 g (ca. 0.04 mole) of anhydrous potassium carbonate;

1'-(2-allyl)-(1RS,2RS,4SR)-spiro[norbornane-2,3'-piperidine] and its hydrochloride, M.P. 246°–247° (from methanol/ether), starting with 6.4 g (0.039 mole) of (1RS,2RS,4SR)-spiro [norbornane-2,3'-piperidine], 3.4 g (0.044 mole) of allyl chloride and 6.2 g (ca. 0.045 mole) of anhydrous potassium carbonate;

1'-isopropyl-(1RS,2RS,4SR)-spiro[norbornane-2,3'piperidine] and its hydrochloride, M.P. 187°–190° (from methanol/ether), starting with 6.4 g (0.039 mole) of (1RS,2RS,4SR)spiro[norbornane-2,3'-piperidine], 5.4 g (0.044 mole) of isopropyl bromide and 6.2 g (ca. 0.045 mole) of anhydrous potassium carbonate;

1'-(3-phenylpropyl)-(1RS,2RS,4SR)-spiro[norbornane-2,3'-piperidine] and its hydrochloride, M.P. 227°–228° (from methanol/ether), starting with 6.4 g (0.039 mole) of (1RS,2RS,4SR)-spiro[norbornane-2,3'-piperidine], 8.8 g (0.044 mole) of 3-phenylpropyl bromide and 6.2 g (ca. 0.045 mole) of anhydrous potassium carbonate;

1'-(3,4-dichlorobenzyl)-(1RS,2RS,4SR)-spiro[norbornane2,3'piperidine] and its hydrochloride, M.P. 240°–245° (from methanol/ether), starting with 4.9 g (0.030 mole) of (1RS,2RS,4SR)-spiro[norbornane-2,3'-piperidine], 6.65 g (0.033 mole) of 3,4-dichlorobenzyl chloride and 4.55 g (0.033 mole) of anhydrous potassium carbonate;

1'-[2-(dimethylamino)-ethyl]-(1RS,2RS,4SR)-spiro[norbornane2,3'-piperidine] and from this, with excess fumaric acid, its difumarate, M.P. 290° (from methylene chloride/ether), starting with 4.1 g (0.025 mole) of (1RS,2RS,4SR)-spiro [norbornane-2,3'-piperidine], 4.3 g (0.03 mole) of 2-(dimethylamino)-ethyl chloride hydrochloride and 10 g (ca. 0.07 mole) of anhydrous potassium carbonate.

EXAMPLE 7

2.93 g (0.0177 mole) of (1RS,2RS,4SR)-spiro[norbornane-2,3'-piperidine], 3.65 g (0.0197 mole) of α-methylbenzyl bromide and 3.43 g of diisopropylethylamine are dissolved in 60 ml of benzene, and the solution stirred for ca. 14 hours at room temperature. The reaction mixture is then washed six times with water, and the aqueous phases in each case separately extracted with 50 ml of ether each time. The combined organic phases are dried over sodium sulphate and concentrated in vacuo (ca. 12 Torr). The base remaining is dissolved in ether and an addition made to the solution, with stirring, of 6 ml of saturated ethereal hydrogen chloride solution. The precipitated hydrochloride is filtered off and recrystallised from acetone to obtain 1'-(α-methylbenzyl)-(1RS,2RS,4SR)-spiro-[norbornane-2,3'-piperidine] hydrochloride-hemihydrate, M.P. 198°–200°.

EXAMPLE 8

An amount of 5 g (0.030 mole) of 1RS,2RS,4SR)-spiro [norbornane-2,3'-piperidine] is dissolved in a mixture of 4.15 g (0.09 mole) of 90% formic acid and 30 ml (ca. 0.4 mole) of 35% aqueous formaldehyde solution, and the solution stirred for 14 hours at 100°. After cooling, the mixture is rendered alkaline with 50 ml of 20% sodium hydroxide solution, and extracted three times with 50 ml of ether each time. The ether extracts are separately washed twice with in each case saturated sodium chloride solution, dried oversodium sulphate and concentrated in vacuo (ca. 12 Torr).

The residue is converted, analogously to Example 4, into the fumarate. There is obtained 1'-methyl-(1RS,2RS,4SR)-spiro[norbornane-2,3'-piperidine]-fumarate (1:1), M.P. 184°–187°.

EXAMPLE 9

An amount of 8.9 g (0.03362 mole) of 1'-[2-(dimethylamino)-acetyl]-spiro[bicyclo[2.2.2]octane-2,3'-piperidine] is dissolved in 300 ml of abs. ether; the solution is then added dropwise in the course of 10 minutes, with stirring, to a mixture of 2.6 g (0.0685 mole) of lithium aluminium hydride in 100 ml of abs. ether. After completed addition, the mixture is refluxed under nitrogen for ca. 14 hours. There are then made to the mixture, cooled with ice water, successive additions dropwise of 2.6 ml of water, 5.2 ml of 2N sodium hydroxide solution and 5.2 ml of water. After subsequent stirring for one hour, the mixture is filtered under reduced pressure, and the filter residue afterwards thoroughly washed with ether. The filtrate is dried over sodium sulphate and then concentrated in vacuo (ca. 12 Torr). The residue is dissolved in 50 ml of abs. benzene and this solution again concentrated by evaporation. This procedure is repeated twice to effect removal of residual traces of moisture; there is thus obtained crude 1'-[2-(dimethylamino)-ethyl]-spiro [bicyclo[2.2.2]octane-2,3'-piperidine]. There is then added excess ethereal hydrogen chloride solution to obtain 1'-[2-(dimethylamino)-ethyl]-spiro[bicyclo[2.2.2]octane2,3'-piperidine]-dihydrochloride, M.P. 295° (with decomposition).

The following are obtained in an analogous manner:
1'-(2-piperidinoethyl)-spiro[bicyclo[2.2.2]octane-2,3'-piperidine]-dihydrochloride, M.P. 280° (from methanol/ether), starting with 9.4 g (0.0309 mole) of 1'-(2-piperidinoacetyl)-spirobicyclo[2.2.2]octane-2,3'-piperidine] and 2.4 g (0.0632 mole) of lithium aluminium hydride;

1'-[2-(1-pyrrolidinyl)-ethyl]-spiro[bicyclo[2.2.2]octane-2,3'-piperidine] and its dihydrochloride, M.P.

300°–305° (from methanol/ether), starting with 6.8 g (0.0241 mole) of 1'-[2-(1-pyrrolidinyl)-acetyl]-spiro[bicyclo[2.2.2] octane-2,3'-piperidine] and 1.9 g (0.05 mole) of lithium aluminium hydride;

1'-[2-(benzylmethylamino)-ethyl]-spiro[bicyclo[2.2.2]octane-2,3'-piperidine] and its dihydrochloride, M.P. 275°–280° (from methanolether), starting with 12 g (0.0357 mole) of 1'-[2-(benzylmethylamino)-acetyl]-spiro[bicyclo[2.2.2] octane-2,3'-piperidine] and 2.8 g (0.0737 mole) of lithium aluminium hydride.

The 1'-[2-(dimethylamino)-acetyl]-spiro[bicyclo[2.2.2] octane-2,3'-piperidine] serving as starting material is produced as follows:

a. An amount of 20 g (0.244 mole) of sodium acetate and 18 g (0.100 mole) of spiro[bicyclo[2.2.2]octane2,3'-piperidine] is dissolved in 100 ml of water and 300 ml of acetone. A two-phase system is formed, to which is added dropwise at 0° to 5° an amount of 10.2 ml (14.4 g, 0.13 mole) of chloroacetyl chloride. An addition is then made to the mixture, at 0° to 5°, of 700 ml of water, whereupon the reaction product precipitates in flake form. Stirring is maintained for a further hour and the reaction product subsequently filtered off. After washing and then drying of the product over phosphorus pentoxide in a desiccator, there is obtained 1'-chloroacetyl-spiro [bicyclo[2.2.2]octane-2,3'-piperidine], M.P. 63° (with decomposition).

b. 8.8 g (0.034 mole) of 1'-chloroacetyl-sprio[bicyclo [2.2.2]octane-2,3'-piperidine] is dissolved in 60 ml of a solution of 10% dimethylamine in benzene, and the solution stirred for ca. 14 hours at room temperature. The mixture is washed six times with water; the aqueous phases are in each case separately extracted twice with 50 ml of ether each time. The organic phases are dried over sodium sulphate and concentrated in vacuo (ca. 12 Torr). The crude 1'-[2-(dimethylamino)-acetyl]-spiro[bicyclo [2.2.2]octane-2,3'-piperidine] is obtained as colourless oil.

Also the following starting materials are obtained analogously to (b):

1'-(2-piperidinoacetyl)-spiro[bicyclo[2.2.2]octane-2,3'-piperidine] as a clear oil from 5.5. g (0.0216mole) of 1'-chloroacetyl-spiro[bicyclo[2.2.2]octane-2,3'-piperidine] and 2.9 g (0.034 mole) of piperidine;

1'-[2-(1-pyrrolidinyl)-acetyl]-spiro[bicyclo[2.2.2]octane-2,3'-piperidine] as colourless oil, from 6.0 g (0.024 mole) 1'-chloroacetyl-spiro[bicyclo[2.2.2]octane-2,3'-piperidine] and 6.8 g (0.096 mole) of pyrrolidine;

1'-[2-(benzylmethylamino)-acetyl]-spiro[bicyclo[2.2.2] octane-2,2'-piperidine] as colourless oil, from 9.1 g (0.0357 mole) of 1'-chloroacetyl-spiro[bicyclo[2.2.2] octane-2,3'-piperidine] and 12.1 g (0.10 mole) of benzylmethylamine.

EXAMPLE 10

There is obtained, analogously to Example 9, 1'-[2-(2-azaspiro[5.5]undec-2-yl)-ethyl]-spiro[bicyclo[2.2.2] octane-2,3'-piperidine]-dihydrochloride, M.P. 260°–270° (from methanol/ether), starting with 4.9 g (0.0132 mole) of 1'-[2-(2-azaspiro[5.5]undec-2-yl)-acetyl]-spiro [2.2.2]octane-2,3'-piperidine] and 0.5 g (0.0632 mole) of lithium aluminium hydride.

The starting material is obtained as clear oil, analogously to Example 9 (b), from 5.9 g (0.023 mole) of 1'-(chloroacetyl)-spiro[bicyclo[2.2.2]octane-2,3'-piperidine] and 3.5 g (0.023 mole) of 2-azaspiro[5.5]undecane [R. C. Schreyer, J. Amer. Chem. Soc. 74, 3194 (1952)], with the addition of 5 ml of triethylamine as additional acid-binding agent instead of excess dimethylamine.

EXAMPLE 11

There are obtained, analogously to Example 9, 1'-[3-(1RS,2RS,4SR)-spiro[norbornane-2,3'-piperidin]-1'-yl)-propyl]-spiro[bicyclo[2.2.2]octane-2,3'-piperidine and its dihydrochloride-hydrate, M.P. 290°–292° (from methanol/ether), starting with 7.1 g (0.0179 mole) of 1'-[3-((1RS,2RS,4SR)-spiro[norbornane-2,3'-piperidin]-1'-yl)-propionyl]-spiro[bicyclo[2.2.2]octane-2,3'-piperidine] and 0.7 g (0.0179 mole) of lithium aluminium hydride.

The starting material is produced as follows:

a. An amount of 2.0 g (0.0112 mole) of spiro[bicyclo[2.2.2]octane-2,3'-piperidine] is added, with ice cooling and with stirring, to a suspension of 2.4 g of sodium acetate in 30 ml of acetone and 10 ml of water; there is then added dropwise to the formed mixture at 0°–5° 1.8 g (0.014 mole) of 3-chloropropionyl chloride. An addition is subsequently made to the mixture, at 0°–5°, of 70 ml of water, whereupon the reaction product precipitates in liquid form. The mixture is extracted three times with 50 ml of methylene chloride each time. The methylene chloride extracts are washed separately in each case once with saturated sodium bicarbonate solution and twice with water; they are then dried over sodium sulphate and afterwards concentrated in vacuo (ca. 12 Torr) to obtain 1'-(3-chloropropionyl)-spiro[bicyclo[2.2.2]octane-2,3'-piperidine].

b. 4.8 g (0.0178 mole) of 1'-(3-chloropropionyl)-spiro[bicyclo[2.2.2]octane-2,3'-piperidine] is dissolved in 50 ml of abs. benzene; an addition is then made of 3.0 g (0.018 mole) of (1RS,2RS,4SR)-spiro[norbornane-2,3'-piperidine] (see Example 2) and 3.5 g (0.0267 mole) of diisopropylethylamine, and the whole refluxed in a nitrogen atomosphere, with stirring, for 42 hours. The mixture is concentrated in vacuo under 12 Torr, and the residue distributed between 50 ml each of water and of chloroform. After separation of the chloroform extract, the aqueous phase is subsequently extracted again with 50 ml of chloroform. The chloroform extracts are washed separately twice with 50 ml of water each time; they are then dried over sodium sulphate and concentrated in vacuo (ca. 12 Torr). There is thus obtained crude 1'-[3-(1RS,2RS,4SR)-spiro[norbornane-2,3'-piperidin]-1'-yl)-propionyl]-spiro[bicyclo[2.2.2]octane-2,3'-piperidine] as colourless oil.

EXAMPLE 12

There are obtained, analogously to Example 9, 1'-[3-(benzylmethylamino)-propyl]-spiro[2.2.2]octane-2,3'-piperidine] and its dihydrochloride-hydrate, M.P. 246°–248° (from methanol/ether), starting with 13.2 g (0.0372 mole) of 1'-[3-(benzylmethylamino)-propionyl]-spiro[bicyclo [2.2.2]octane-2,3'-piperidine] and 1.4 g (0.036 mole) of lithium aluminium hydride.

a. The starting material: 1'-[3-(benzylmethylamino)-propionyl]-spiro[bicyclo[2.2.2]octane-2,3'-piperidine], is obtained as clear oil, analogously to Example 11 (b), from 1.0 g (0.0372 mole) of 1'-(3-chloropropionyl)-spiro [bicyclo[2.2.2]octane-2,3'-piperidine] [cp. Example 11 a)] and 5.9 g (0.0488 mole) of N-methylbenzylamine.

EXAMPLE 13

An amount of 2.68 g (0.0123 mole) of spiro[bicyclo [2.2.2]octane-2,3′-piperidine]-1′-acetonitrile is dissolved in 25 ml of abs. ether, and the solution stirred, within 15 – 20 minutes with ice cooling, into a suspension of 0.63 g (0.0165 mole) of lithium aluminium hydride in 75 ml of abs. ether. The mixture is refluxed in a nitrogen atmosphere for 16 hours. After cooling, dropwise additions are made successively of 1 ml of water, 2 ml of 2N sodium hydroxide solution and a further 1 ml of water. The mixture is then stirred for one hour at room temperature, filtered under reduced pressure, and the filter residue subsequently thoroughly washed with ether. The filtrate is dried over sodium sulphate and concentrated by evaporation. There is thus obtained 1′-(2-aminoethyl)-spiro[bicyclo[2.2.-2]octane-2,3′-piperidine], which is converted with excess ethereal hydrogen chloride solution into 1′-(2-aminoethyl)-spiro[bicyclo[2.2.2]octane-2,3′-piperidine]-dihydrochloride, M.P. 270°–272° (from methanol/ether).

a. The spiro[bicyclo[2.2.2]octane-2,3′-piperidine]-1′-acetonitrile serving as starting material is produced analogously to Example 5, starting with 7.1 g (0.040 mole) of spiro[bicyclo[2.2.2]octane-2,3′-piperidine], 3.6 g (0.048 mole) of chloroacetonitrile and 10 g (ca. 0.07 mole) of anhydrous potassium carbonate.

EXAMPLE 14

4.45 g (0.020 mole) of 1′-(2-aminoethyl)-spiro[bicyclo [2.2.2]octane-2,3′-piperidine] is heated in a mixture of 5.5 g (0.12 mole) of 90% formic acid and 40 ml (ca. 0.53 mole) of 35% aqueous formaldehyde solution, with stirring, for 14 hours at 100°. After cooling, the mixture is rendered alkaline with 60 ml of 20% sodium hydroxide solution, and extracted three times with 50 ml of ether each time. The ether extracts are washed separately in each case twice with saturated sodium chloride solution, dried over sodium sulphate and dried in vacuo (ca. 12 Torr). The residue is dissolved in 50 ml of abs. benzene; this is then evaporated off and the treatment with benzene repeated twice. The crude 1′-[2-(dimethylamino)-ethyl]-spiro[bicyclo[2.2.2]octane-2,3′-piperidine] remaining behind is converted, with excess ethereal hydrogen chloride solution, into its dihydrochloride, M.P. 295° (with decomposition).

EXAMPLE 15

24.9 g (0.15 mole) of (1RS,2RS,4SR)-spiro[norbornane-2,3′-piperidine] and 25 g of potassium carbonate are suspended in 100 ml of ethanol; an addition of 15.0 g (0.11 mole) of epichlorohydrin (1-chloro-2,3-epoxy-propane) is subsequently made, whereupon the mixture heats up to 40°. It is stirred for 16 hours at room temperature and then concentrated in vacuo (ca. 12 Torr). The residue is suspended in 150 ml of water, and extracted three times with 50 ml of chloroform each time. The chloroform extracts are washed separately three times with 50 ml of water each time, dried over sodium sulphate and concentrated by evaporation. The residue is dissolved in 200 ml of 2N hydrochloric acid; this solution is extracted once with 50 ml of chloroform and concentrated in vacuo (ca. 12 Torr). The obtained reddish crystals are recrystallised from acetone/ether to obtain α-(chloromethyl)-(1RS,2RS,4SR)-spiro[norbornane-2,3′-piperidine]-1′-ethanol-hydrochloride, M.P. 199°–201°.

EXAMPLE 16

An amount of 0.6 g (0.026 gram atom) of sodium is dissolved in 150 ml of ethanol; successive additions are then made, to the obtained sodium ethoxide solution, of 5.2 g (0.02 mole) of α-(chloromethyl)-(1RS,2RS,4SR)-spiro[norbornane-2,3-piperidine]-1′-ethanol (see Example 15) and 3.5 g of (1RS,2RS,4SR)-spiro[norbornane-2,3′-piperidine]. The reaction mixture is subsequently refluxed in a nitrogen atmosphere for 16 hours and, after cooling, concentrated in vacuo (ca. 12 Torr). The residue is suspended with 150 ml of water and extracted three times with 50 ml of chloroform each time. The chloroform extracts are separately washed twice with water; they are then dried over sodium sulphate, and concentrated in vacuo (ca. 12 Torr) to obtain 1,3-bis-((1RS,2RS,4SR)-spiro [norbornane-2,3′-piperidin]-1′-yl)-2-propanol. This is converted with excess ethereal hydrogen chloride into the dihydrochloride which, after recrystallisation from methanol/ether melts at 160° (with decomposition).

What we claim is:

1. An antiviral pharmaceutical composition comprising an antivirally effective amount of a heterocyclic spiro compound

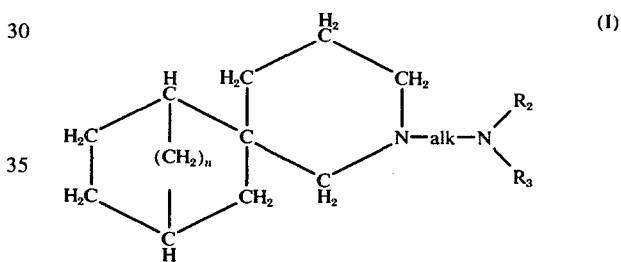

in which alk represent ethylene, trimethylene or 2-hydroxytrimethylene, $R_2$ represents hydrogen, methyl or benzyl, $R_3$ represents hydrogen or methyl, or $R_2$ and $R_3$ together represent tetramethylene, pentamethylene, 2,2-pentamethylene-pentamethylene, or 2,2-(1,4-methanopentamethylene)-pentamethylene and n denotes 1 or 2, or of a pharmaceutically acceptable acid addition salt thereof together with a pharmaceutically acceptable carrier.

2. An antiviral pharmaceutical composition according to claim 1 comprising an antivirally effective amount of 1′-[2-(2-azaspiro[5.5]undec-2-yl)-ethyl]-spiro[bicyclo[2.2.2] octane-2,3′-piperidine] or of a pharmaceutically acceptable acid addition salt thereof together with a pharmaceutically acceptable carrier.

3. An antiviral pharmaceutical composition according to claim 1 comprising an antivirally effective amount of 1′-[2-(2-azaspiro[5.5]undec-2-yl)-ethyl]-spiro[bicyclo[2.2.2]octane-2,3′-piperidine] dihydrochloride together with a pharmaceutically acceptable carrier.

4. The method of producing an antiviral effect in a mammal which comprises administering to said mammal an antivirally effective amount of a heterocyclic spiro compound having the formula I given in claim 1, wherein $R_2$, $R_3$, alk and n have the meanings defined in claim 1, or of a pharmaceutically acceptable acid addition salt thereof.

5. The method according to claim 4 which comprises administering to a mammal an antivirally effective amount of 1'-[2-(2-azaspiro[5.5]undec-2-yl)-ethyl]-spiro[bicyclo[2.2.2] octane-2,3'-piperidine] or of a pharmaceutically acceptable acid addition salt thereof.

6. The method according to claim 4 which comprises administering to a mammal an antivirally effective amount of 1'-[2-(azaspiro[5.5]undec-2-yl)-ethyl]-spiro[bicyclo[2.2.2] octane-2,3'-piperidine]dihydrochloride.

* * * * *